(12) United States Patent
Salmon

(10) Patent No.: US 6,274,632 B1
(45) Date of Patent: Aug. 14, 2001

(54) DERIVATIVES OF 4,4-DIFLUOROBUT-3-ENYLSULFINIC ACID AND THEIR USE AS PESTICIDES

(75) Inventor: Roger Salmon, Bracknell (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/380,912

(22) PCT Filed: Mar. 4, 1998

(86) PCT No.: PCT/GB98/00692

§ 371 Date: Sep. 10, 1999

§ 102(e) Date: Sep. 10, 1999

(87) PCT Pub. No.: WO98/40352

PCT Pub. Date: Sep. 17, 1998

(30) Foreign Application Priority Data

Mar. 12, 1997 (GB) .................................................. 9705120

(51) Int. Cl.$^7$ ..................... A61K 31/535; A61K 31/495; A61K 31/445; A61K 31/255; A61K 31/10

(52) U.S. Cl. ................. 514/708; 514/231.2; 514/252.12; 514/315; 514/517; 544/158; 544/383; 546/184; 558/61; 562/125; 562/825; 562/827; 564/101

(58) Field of Search ................................. 514/231.2, 315, 514/517, 708, 252.12; 544/158, 383; 546/184; 558/61; 562/125, 825, 827; 564/101

(56) References Cited

U.S. PATENT DOCUMENTS

| 3,463,803 | 8/1969 | Aichenegg | 260/453 |
|---|---|---|---|
| 3,764,698 | * 10/1973 | Partos | 424/303 |
| 3,885,951 | * 5/1975 | Hofer et al. | 71/103 |

* cited by examiner

*Primary Examiner*—Peter O'Sullivan

(57) ABSTRACT

The invention relates to compounds of the formula (I): $CF_2=CX-CH_2-CH_2-S(O)-R$ wherein X represents hydrogen, halogen or lower alkyl, and R represents a group $OR^1$ or $NR^2R^3$ wherein $R^1$, $R^2$ and $R^3$ are as defined in the description. The compounds are useful for controlling insect and like pests of agriculture.

12 Claims, No Drawings

DERIVATIVES OF 4,4-DIFLUOROBUT-3-ENYLSULFINIC ACID AND THEIR USE AS PESTICIDES

This application is a 371 of PCT/GB98/00692 filed Mar. 4, 1998.

This invention relates to sulfur containing acids and their derivatives, and more particularly to sulfur-containing acids and salts, esters and amides thereof having utility as pesticidal agents.

In a first aspect the invention provides compounds of formula (I):

$$CF_2=CX-CH_2-CH_2-S(O)-R \qquad (I)$$

wherein X represents hydrogen, halogen or lower alkyl, and R represents a group $OR^1$ or $NR^2R^3$ wherein $R^1$, $R^2$ and $R^3$ are each independently selected from hydrogen and alkyl, alkenyl, alkynyl, cycloalkyl, aryl, aralkyl, alkaryl, heteroaryl. and heteroarylalkyl groups, or $R^2$ and $R^3$ together with the adjacent nitrogen atom and wherein any of the groups represented by $R^1$, $R^2$ and $R^3$ may optionally be substituted by one or more substituents selected from halogen, cyano, nitro, hydroxy, hydrocarbyloxy, amino, hydrocarbylamino, dihydrocarbylamino, carboxy, hydrocarbyloxycarbonyl, carboxamido, hydrocarbylaminocarbonyl, dihydrocarbylaminocarbonyl, hydrocarbylthio, hydrocarbylsulfinyl, and hydrocarbylsulfonyl, wherein any such hydrocarbyl groups may optionally be substituted by one or more substituents as aforesaid; and salts thereof.

Preferred compounds are those where X is hydrogen, fluorine or methyl.

Where any of $R^1$, $R^2$ and $R^3$ represent groups comprising carbon atoms they prefereably contain up to 12 carbon atoms, and more preferably, except in the case of aryl, aralkyl and alkaryl groups, up to 6 carbon atoms.

Examples of groups of formula $NR^2R^3$ which represent a nitrogen containing heterocyclic group which may contain a further heteroatom selected from oxygen, sulfur and nitrogen, include for example piperidine, piperazine, morpholine, thiazolidine, imidazoline, and the like.

Salts of the compounds of Formula (I) may be, in the case where $R^1$ is hydroxy, or where $R^1$, $R^2$ or $R^3$ represents a group comprising an acidic hydrogen, metal salts, including for example, sodium, potassium, calcium, magnesium, copper, zinc or iron, or ammonium salts, amine salts or quaternary ammonium salts.

Specific examples of compounds according to the present invention include those set out in Tables I and IA below.

TABLE I

| Compound no. | X | $R^1$ | $R^2$ | $R^3$ |
|---|---|---|---|---|
| 1 | H | H | — | — |
| 1A | H | Na | — | — |
| 2 | H | $C_2H_5$ | — | — |
| 3 | H | $n-C_6H_{13}$ | — | — |
| 4 | H | — | H | H |
| 5 | H | — | H | $CH_3$ |
| 6 | F | H | — | — |
| 7 | F | $n-C_4H_9$ | — | — |
| 8 | F | — | H | H |
| 9 | F | — | $C_2H_5$ | $C_2H_5$ |
| 10 | $CH_3$ | H | — | — |
| 11 | H | $CH_2C_6H_5$ | — | — |
| 12 | H | $n-C_8F_{17}$ | — | — |
| 13 | H | cyclo-$C_6H_{11}$ | — | — |
| 14 | H | — | H | $C_6H_5CH_2$ |
| 15 | H | — | $3-Cl-C_6H_4$ | H |
| 16 | H | $CH_2CF_3$ | — | — |
| 17 | H | $(CH_2)_2CH=CF_2$ | — | — |
| 18 | H | $CH_2CH_2OC_2H_5$ | — | — |
| 19 | F | $CH_2CH=CH_2$ | — | — |
| 20 | F | — | H | $C_6H_5CH_2$ |
| 21 | H | — | H | $4-Cl-C_6H_4CH_2$ |

TABLE IA

| Compound No | X | $NR^2R^3$ |
|---|---|---|
| 22 | H | morpholinyl |
| 23 | H | 4-methylpiperazinyl |
| 24 | F | piperidinyl |

The compounds of Formula (I) may be prepared as follows. For convenience the group $CF_2=CX-CH_2-CH_2-$ is represented in the following description by Q.

Compounds where R represents hydroxy are sulfinic acids and may be prepared for example by reducing the corresponding sulfonyl chloride of formula $Q-SO_2Cl$, or by reducing the corresponding benzthiazol-2-yl sulphone using the conditions described in Chem.Lett. 2125 (1984) via the sodium salt. Another method of preparation involves reacting the Grignard reagent of formula $Q-Mg-Cl$ with sulfur dioxide using the conditions set out in Chem. Revs. 48 69 (1950).

Compounds where R represents $OR^1$ may be prepared by esterification of the sulfinic acids under mild conditions, such as those described in Synthesis, p441 (1978), or via the sulfinyl chlorides, prepared by treating the acids with thionyl chloride or oxalyl chloride, and reaction with alcohols of formula $R^1OH$. Another method involves treating the disufide of formula $Q-S-S-Q$ with a peroxy compound in in the presence of an alcohol as described in Synthesis, p252 (1988). A yet further process treats the sulfonyl chloride of formula $Q-SO_2Cl$ with an alcohol under reducing conditions, for example in the presence of trimethyl phosphinate, as described in J. Org. Chem. 52 2598 (1987).

Compounds where R represents $NR^2R^3$ may be prepared by reacting the sulfinyl chlorides of formula $Q-S(O)Cl$ with a compound of formula $NHR^2R^3$.

The sulfinyl chlorides (and other halides) useful in the preparation of the compounds of formula (I) as described herein are novel compounds. In a further aspect the invention provides compounds of formula (II):

$$CF_2=CX-CH_2-CH_2-S(O)-Y \qquad (II)$$

where X is hydrogen or halogen or lower alkyl, preferably hydrogen or fluorine, and Y is halogen, preferably chlorine, useful as intermediates for preparing the compounds of formula (I). Specific examples of compounds of formula (II) include 1-(4,4-difluorobut-3-ene)sulfinyl chloride and 1-(4,4-trifluorobut-3-ene) sulfinyl chloride.

Further information concerning the preparation of individual compounds may be ascertained from the Examples given hereinafter.

In a further aspect the invention provides a method of combating insect and like pests at a locus by applying to the locus or the pests an insecticidally-effective amount of an insecticidal composition comprising the compounds of Formula I or an acid addition salt thereof.

The compounds of Formula I and acid addition salts thereof may be used to combat and control infestations of insect pests such as Lepidoptera, Diptera, Homoptera and Coleoptera (including Diabrotica i.e. corn rootworms) and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals. Examples of insect and acarine pest species which may be controlled by the compounds of Formula I include:

Myzus persicae (aphid), Aphis gossypii (aphid), Aphis fabae (aphid), Aedes aegypti (mosquito), Anopheles spp. (mosquitos), Culex spp. (mosquitos), Dysdercus fasciatus (capsid), Musca domestica (housefly), Pieris brassicae (white butterfly), Plutella xlostella (diamond back moth), Phaedon cochleariae (mustard beetle), Aonidiella spp. (scale insects), Trialeurodes spp. (white flies), Bemisia tabaci (white fly), Blattella germanica (cockroach), Periplaneta americana (cockroach), Blatta orientalis (cockroach) Spodoptera littoralis (cotton leafworm), Heliothis virescens (tobacco budworm) Chortiocetes terminifera (locust), Diabrotica spp. (rootworms), Agrotis spp. (cutworms), Chilo partellus (maize stem borer), Nilaparvata lugens (planthopper), Nephotettix cincticeps (leafhopper), Panonychus ulmi (European red mite), Panonychus citri (citrus red mite), Tetranychus urticae (two-spotted spider mite), Tetranychus cinnabarinus (carmine spider mite), Phyllcoptruta oleivora (citrus rust mite), Polyphagotarsonemus latus (broad mite) and Brevipalpus spp. (mites).

In order to apply the compounds of Formula I to the locus of the nematode, insect or acarid pest, or to a plant susceptible to attack by the nematode, insect or acarid pest, the compound is usually formulated into a composition which includes in addition to the the compounds of Formula I suitable inert diluent or carrier materials, and/or surface active agents. The amount of composition generally applied for the control of nematode pests gives a rate of active ingredient from 0.01 to 10 kg per hectare, preferably from 0.1 to 6 kg per hectare.

The compositions can be applied to the soil, plant or seed, to the locus of the pests, or to the habitat of the pests, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropyl- naphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of Formula I may also be formulated as powders (dry seed treatment DS or water dispersible powder WS) or liquids (flowable concentrate FS, liquid seed treatment LS, or microcapsule suspension CS) for use in seed treatments.

In use the compositions are applied to the insect pests, to the locus of the pests, to the habitat of the pests, or to growing plants liable to infestation by the pests, by any of the known means of applying pesticidal compositions, for example, by dusting, spraying, or incorporation of granules.

The compound of Formula I may be the sole active ingredient of the composition or they may be admixed with one or more additional active ingredients such as insecticides, synergists, herbicides, fungicides or plant growth regulators where appropriate.

Suitable additional active ingredients for inclusion in admixture with a compound of Formula I may be compounds which will broaden the spectrum of activity of the compositions of the invention or increase their persistence in the location of the pest. They may synergise the activity of the compound of Formula I or complement the activity for example by increasing the speed of effect or overcoming repellency. Additionally multi-component mixtures of this type may help to overcome or prevent the development of resistance to individual components. The particular additional active ingredient included will depend upon the intended utility of the mixture and the type of complementary action required. Examples of suitable insecticides include the following:
a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;
b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;
c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;
d) Benzoyl ureas such as triflumuron, or chlorfluazuron;
e) Organic tin compounds such as cyhexatin, fenbutatin oxide, azocyclotin;
f) Macrolides such as avermectins or milbemycins, for example such as abamectin, ivermectin, and milbemycin;
g) Hormones and pheromones;
h) Organochlorine compounds such as benzene hexachloride, DDT, chlordane or dieldrin;
i) Amidines, such as chlordimeform or amitraz;
j) Fumigant agents;
k) Imidacloprid.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, motilicides such as dicofol or propargite, acaricides such as bromopropylate, chlorobenzilate, or growth regulators such as hydramethylron, cyromazine, methoprene, chlorofluazuron and diflubenzuron may also be included in the compositions. up Examples of suitable synergists for use in the compositions include piperonyl butoxide, sesamax, safroxan and dodecyl imidazole. Suitable herbicides, fungicides and plant-growth regulators for inclusion in the compositions will depend upon the intended target and the effect required.

An example of a rice selective herbicide which can be included is propanil, an example of a plant growth regulator for use in cotton is "Pix", and examples of fungicides for use in rice include blasticides such as blasticidin-S. The ratio of the compounds of Formula I to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The invention is illustrated by the following examples. Examples 1 to 3 illustrate the preparation of compounds of formula (I). Examples 4 to 11 illustrate pesticidal compositions suitable for the application of the the compounds of Formula I. The following ingredients are referred to by their Registered Trade Marks and have the composition as shown below.

| Registered Trade Mark | Composition |
|---|---|
| Synperonic NP8 } | Nonylphenol ethylene oxide |
| Synperonic NP13 } | condensate |
| Synperonic OP10 } | |
| Aromasol H | Alkylbenzene solvent |
| Solvesso 200 | Inert organic diluent |
| Keltrol | Polysaccharide |

EXAMPLE 1

This illustrates a preparation of bis-(4,4-difluorobut-3-enyl)disulfide

Step 1: Preparation of 1,4-dibromo-1,1,2-trifluorobutane.

4-Bromo-1,1,2-trifluorobut-1-ene (Fluorochem Ltd.) (240 g) was washed with water (300 cm$^3$) and then with brine (300 cm$^3$) and dried (MgSO$_4$) before use. Benzoyl peroxide (ca. 0.7 g) was added in one portion and hydrogen bromide gas was bubbled through the mixture at such a rate that the reaction temperature was maintained at 30 to 40° C. After 2 hours, gc of a sample of the reaction mixture showed that little starting material remained. The reaction mixture was washed with water (300 cm$^3$), then with saturated sodium bicarbonate solution and then again with water (300 cm$^3$), dried (MgSO$_4$), and filtered to give a pale yellow oil (296.7 g) identified as 1,4-dibromo-1,1,2-trifluorobutane. The material was shown by gc analysis to be greater than 98% pure. $^1$H NMR: δ2.38(2H,m); 3.57(2H,m); 4.90(1H,m).

Step 2: Preparation of 4-bromo-1,1-difluorobut-1-ene

Zinc powder (0.88 g) was added to a stirred solution of 1,4-dibromo-1,1,2-trifluorobutane (1.38 g) in acetone (6 cm$^3$) containing water (1 drop), under an atmosphere of nitrogen. After 45 minutes, gc analysis showed that a large proportion of the starting material had been consumed. The mixture was then added to more zinc powder (3 g) in acetone containing a trace of water, which had been preheated to 55° C. After a further 20 minutes at this temperature, gc analysis indicated that all of the starting material had been consumed, showing that the de-bromofluorination reaction had initiated. More starting material (12.34 g) was then added to the reaction over a period of 75 minutes while the reaction mixture was kept at 55° C. Heating was then continued for a further 95 minutes. GC analysis of a sample indicated that about 3% of the starting dibromo compound remained unchanged. Further zinc powder (0.16 g) was added and heating continued until gc analysis showed all the starting material had been consumed. The acetone solution was decanted from the zinc residues to give a solution of 4-bromo-1,1-difluorobut-1-ene suitable for use in further chemical reactions.

Step 3: Preparation of bis(4,4-difluorobut-2-enyl)disulfide.

A solution of sodium disulfide (previously prepared from sodium sulfide nonahydrate (53 g) and sulfur (7.0 g) in ethanol (250 cm$^3$)) was added to 1-bromo4,4-difluorobut-3-ene (50 g) in ethanol (100 cm$^3$). The mixture was gradually heated and stirred under reflux for 2 hours, then cooled and evaporated under reduced pressure. The residue was extracted with diethyl ether, the organic phase filtered to remove sodium bromide and the ether evaporated under reduced pressure to give a liquid which was distilled at 16 mm Hg, bp 120° C. to give the bis-(4,4-difluorobut-3-enyl) disulfide (24 g) as a colourless liquid.

EXAMPLE 2

This example illustrates the preparation of n-hexyl 4,4-difluorobut-3-enyl-sulfinate Bis(4,4-difluorobut-3-enyl) disulfide (1.0 g) in n-hexanol (10 cm$^3$) was stirred with potassium carbonate (anhydrous, 0.54 g) under an atmosphere of nitrogen and cooled to 0° C. To the mixture was added N-bromosuccinimide (2.0 g) and the reaction allowed to warm to ambient temperature over 1.5 h. The reaction was extracted into diethyl ether (150 cm$^3$), washed with water (2×100 cm$^3$), dried (magnesium sulfate) and the solvent removed by evaporation under reduced pressure. The oil obtained was evaporated under reduced pressure (110° C. at 15 mm Hg) to remove the n-hexanol that was present and the residual oil was fractionated by chromatography (silica, dichloromethane) to give the required product as a pale yellow-orange oil, 0.14 g.

$^1$H NMR (CDCl$_3$) 0.90(3H,m); 1.30(6H,m); 1.70(2H,m); 2.45(2H,m); 2.80(2H,m) 4.0(2H,m); 4.25(1H,double triplet of doublets).

Chemical ionisation mass spectrum MNH$_4^+$ molecular ion 258.

EXAMPLE 3

This example illustrates the preparation of 4,4-difluorobut-3-enyl sulfinic acid (as the sodium salt).

Stage 1

2-(4,4-difluorobut-3-enylthio)benzthiazole (prepared by the method described in United Kingdom Patent Application GB2270689A, 8.25 g) in dichloromethane ( 15 cm$^3$) was added to a rapidly stirred mixture of monomagnesium peroxyphthalic acid hexahydrate (25.7 g, 70–80% technical grade) in water (25 cm$^3$). The mixture was stirred for 2 days, diluted with dichloromethane and water, the organic phase separated, washed with aqueous sodium carbonate, water and dried (magnesium sulfate). The solvent was evaporated under reduced pressure to give 2-(4,4-difluorobut-3-enylsulfonyl )benzthiazole as a colourless oil, 4.9 g.

Stage 2

2(4,4-difluorobut-3-enylsulfonyl)benzthiazole (1.9 g) in methanol (13 cm$^3$) was stirred at ambient temperature and treated with sodium borohydride (0.52 g) in portions. The reaction mixture was stirred for 2 h, further sodium borohyride (0.50 g) added and stored at ambient temperature for 18 h. The solution was evaporated under reduced pressure and the residue partioned between water and diethyl ether. The aqueous phase was separated and re-extracted with diethyl ether (2×150 cm$^3$) to remove benzthiazole and the aqueous phase evaporated under reduced pressure to give the required product as a hygroscopic solid.

$^1$H NMR (D$_2$O) 2.22(2H,m); 2.38(2H,m); 4.34(1H,double triplet of doublets).

$^{13}$C NMR (D$_2$O) shifts in ppm (F2C=CH)156; (CH=CF2) 79; (CH2SO$_2$),60; (O2SCH2CH2CH=C),18.

EXAMPLE 4

This example illustrates the preparation of N-4-chlorobenzyl 4,4-difluorobut-3-enyl-sulfinamide Stage 1:

Preparation of 4,4-difluorobut-3-enyl sulfinylchloride.

Thionyl chloride (200 ml) in dry n-hexane (400 ml) was stirred at ambient temperature and 4,4-difluorobut-3-enyl-sulfinic acid sodium salt ( 44 g) was added in portions. On complete addition the mixture was heated to reflux under nitrogen for 4.5 hours, cooled to ambient temperature then filtered. The filtrate was evaporated under reduced pressure to give a liquid which was distilled and the fraction collected at bp 50–60° C. at 0.1 mm Hg to yield 4,4-difluorobut-3-enyl sulfinylchloride (5.6 g). IR(film) n 2946,1725, 1380,1150,730 cms$^{-1}$.

Stage 2:

4,4-Difluorobut-3-enyl sulfinylchloride (0.5 g) in dry diethyl ether (1.5 ml) was stirred at ambient temperature and 4-chlorobenzylamine (1.0 g) in diethyl ether (1.5 ml) was added dropwise. The mixture was stored at ambient temperature for 2 days then water (100 ml) added. The mixture was made acidic with aqueous hydrochloric acid (2M) and extracted with dichloromethane (100 ml). The organic fraction was separated, washed with water then dried over anhydrous magnesium sulfate. The solvent was evaporated under reduced pressure to give an oil which was fractionated by chromatography (silica; ethyl acetate/hexane 2:1 by volume) to give N-4-chlorobenzyl 4,4-difluorobut-3-enyl-sulfinamide, 0.094 g, as an off-white solid, mp37–8° C.

$^1$H NMR (CDCl$_3$) d: 2.38(2H,m); 2.82(2H,m); 4.10(1H,t); 4.25(3H,m); 7.30(4H,m) ppm.

EXAMPLES 5

This Example illustrates an emulsifiable concentrate composition which is readily convertible by dilution with water into a liquid preparation suitable for spraying purposes. The concentrate has the following composition:

|  | % Weight |
|---|---|
| Compound No. 1 | 25.5 |
| SYNPERONIC NP13 | 2.5 |
| Calcium dodecylbenzenenesulphonate | 2.5 |
| AROMASOL H | 70 |

EXAMPLE 6

This Example illustrates a wettable powder composition which is readily convertible by dilution with water into a liquid preparation suitable for spraying purposes. The wettable powder has the following composition:

|  | % Weight |
|---|---|
| Compound No. 13 | 25.0 |
| Silica | 25.0 |
| Sodium lignosulphonate | 5.0 |

-continued

| | % Weight |
|---|---|
| Sodium lauryl sulphate | 2.0 |
| Kaolinite | 43.0 |

EXAMPLE 7

This Example illustrates a dusting powder which may be applied directly to plants or other surfaces and comprises 1% by weight of Compound No. 25 and 99% by weight of talc.

EXAMPLE 8

This Example illustrates a concentrated liquid formulation suitable for application by ultra low volume techniques after mixing with paraffinic diluents.

| | % Weight |
|---|---|
| Compound No. 19 | 90.0 |
| SOLVESSO 200 | 10.0 |

EXAMPLE 9

This Example illustrates a capsule suspension concentrate which is readily convertible by dilution with water to form a preparation suitable for application as an aqueous spray.

| | % Weight |
|---|---|
| Compound No. 4 | 10.0 |
| Alkylbenzene solvent (e.g. AROMASOL H) | 5.0 |
| Toluene di-isocyanate | 3.0 |
| Ethylenediamine | 2.0 |
| Polyvinyl alcohol | 2.0 |
| Bentonite | 1.5 |
| Polysaccharide (e.g. KELTROL) | 0.1 |
| Water | 76.4 |

EXAMPLE 10

A ready for use granular formulation:

| | % Weight |
|---|---|
| Compound No. 1 | 0.5 |
| SOLVESSO 200 | 0.2 |
| nonylphenol ethoxylate (eg Synperonic NP8) | 0.1 |
| Calcium carbonate granules (0.3–0.7 mm) | 99.2 |

EXAMPLE 11

An aqueous suspension concentrate:

| | % Weight |
|---|---|
| Compound No. 21 | 5.0 |
| Kaolinite | 15.0 |

-continued

| | % Weight |
|---|---|
| Sodium lignosulphonate | 3.0 |
| nonylphenol ethoxylate (eg Synperonic NP 8) | 1.5 |
| propylene glycol | 10.0 |
| Bentonite | 2.0 |
| Polysaccharide (eg Keltrol) | 0.1 |
| Bactericide (eg Proxel; Proxel is a registered Trade Mark) | 0.1 |
| Water | 63.3 |

EXAMPLE 12

This Example illustrates a water dispersible granule formulation.

| | % Weight |
|---|---|
| Compound No. 3 | 5 |
| Silica | 5 |
| Sodium lignosulphate | 10 |
| Sodium dioctylsulphosuccinate | 5 |
| Sodium acetate | 10 |
| Montmorillonite powder | 65 |

EXAMPLE 13

This Example illustrates the insecticidal properties of the compounds of Formula I. The activity of the the compounds of Formula I was determined using a variety of pests. The pests were treated with a liquid composition containing 500 parts per million (ppm) by weight of the compound unless otherwise stated. The compositions were made by dissolving the compound in acetone and ethanol (50:50) mixture and diluting the solutions with water containing 0.05% by weight of a wetting agent sold under the trade name "SYNPERONIC" NP8 until the liquid composition contained the required concentration of the compound. "SYNPERONIC" is a Registered Trade Mark.

The test procedure adopted with regard to each pest was basically the same and comprised supporting a number of the pests on a medium which was usually a substrate, a host plant or a foodstuff on which the pests feed, and treating either or both the medium and the pests with the compositions. The mortality of the pests was then assessed at periods usually varying from two to five days after the treatment.

The results of the tests against peach aphid (*Myzus persicae*) are presented below. The results indicate a grading of mortality (score) designated as A, B or C wherein C indicates less than 40% mortality, B indicates 40–79% mortality and A indicates 80–100% mortality. In this test Chinese cabbage leaves were infested with aphids, the infested leaves were sprayed with the test composition, and the mortality assessed after 3 days.

In this test Compounds nos. 1 and 3 gave a grading of A. In similar tests these compounds gave a grading of A against spider mites (*Tetranychus urticae*), and Compound no. 21 gave a grading of B against larval *Heliothis virescens*. In addition Compounds 1,3 and 21 gave a grading of A against nematodes (*Meloidogyne incognita*) when applied at a rate of 12.5 ppm.

What is claimed is:

1. A compound of formula (I):

$$CF_2=CX-CH_2-CH_2-S(O)-R \qquad (I)$$

wherein X represents hydrogen, halogen or lower alkyl, and R represents a group $OR^1$ or $NR^2R^3$ wherein $R^1$, $R^2$ and $R^3$ are each independently selected from hydrogen and alkyl, alkenyl, alkynyl, cycloalkyl, aryl, aralkyl, alkaryl, heteroaryl and heteroarylalkyl groups, or $R^2$ and $R^3$ together with the adjacent nitrogen atom represent a nitrogen containing heterocyclic group which may contain a further heteroatom selected from oxygen, sulfur and nitrogen, and wherein any of the groups represented by $R^1$, $R^2$ and $R^3$ may optionally be substituted by one or more substituents selected from halogen, cyano, nitro, hydroxy, hydrocarbyloxy, amino, hydrocarbylamino, dihydrocarbylamino, carboxy, hydrocarbyloxycarbonyl, carboxamido, hydrocarbylaminocarbonyl, dihydrocarbylaminocarbonyl, hydrocarbylthio, hydrocarbylsulfinyl, and hydrocarbylsulfonyl, wherein any such hydrocarbyl groups may optionally be substituted by one or more substituents as aforesaid; and salts, esters and amides thereof.

2. A compound of Formula (I) according to claim 1 wherein X is hydrogen, fluorine or methyl.

3. A compound of Formula (I) according to claim 1 wherein X is hydrogen or fluorine and $R^1$ is hydrogen; and salts, esters and amides thereof.

4. A compound according to claim 1 selected from 4,4-difluorobut-3-enylsulfinic acid, and salts, esters and amides thereof.

5. 4,4-Difluorobut-3-enylsulfinic acid.

6. N-4-Chlorobenzyl 4,4-difluoro-3-butenylsulfinamide.

7. A compound of formula (II)

$$CF_2=CX-CH_2-CH_2-S(O)-Y \qquad (II)$$

where X is hydrogen or halogen or lower alkyl and Y is halogen.

8. A compound according to claim 7 wherein X is hydrogen and Y is chlorine.

9. A pesticidal composition comprising a pesticidally effective amount of a compound according to claim 1 in association with an agriculturally acceptable liquid or solid diluent material.

10. A method of combating pests at a locus which comprises applying to the locus a pesticidally effective amount of a composition according to claim 9.

11. A method according to claim 10 wherein the pests are insect, acarine or nematode pests of growing plants and the composition is applied to the plants or to the soil in which the plants are growing.

12. A method of controlling soil-inhabiting nematode pests of plants which comprises treating the soil so as to provide a nematode-controlling amount of a compound according to claim 5 or a salt thereof in the soil.

* * * * *